(12) United States Patent
Gemon et al.

(10) Patent No.: US 11,690,725 B2
(45) Date of Patent: Jul. 4, 2023

(54) METHOD FOR PRODUCING A TAILOR-MADE IMPLANT

(71) Applicant: 3D MEDICAL, Marolles-en-Brie (FR)

(72) Inventors: Jean-Pierre Gemon, Bordeaux (FR); Vincent Nuttens, Brunoy (FR)

(73) Assignee: 3D MEDICAL, Marolles-en-Brie (FR)

( * ) Notice: Subject to any disclaimer, the term of this patent is extended or adjusted under 35 U.S.C. 154(b) by 429 days.

(21) Appl. No.: 16/769,383

(22) PCT Filed: Dec. 5, 2018

(86) PCT No.: PCT/FR2018/053117
§ 371 (c)(1),
(2) Date: Jun. 3, 2020

(87) PCT Pub. No.: WO2019/110928
PCT Pub. Date: Jun. 13, 2019

(65) Prior Publication Data
US 2020/0297495 A1    Sep. 24, 2020

(30) Foreign Application Priority Data
Dec. 5, 2017   (FR) ...................................... 17 61629

(51) Int. Cl.
*A61F 2/30*     (2006.01)
*B33Y 50/00*    (2015.01)
(Continued)

(52) U.S. Cl.
CPC ........ *A61F 2/30942* (2013.01); *B29C 64/386* (2017.08); *B33Y 50/00* (2014.12);
(Continued)

(58) Field of Classification Search
CPC ........ A61F 2/30942; A61F 2002/30948; A61F 2002/30952; A61F 2002/30957;
(Continued)

(56) References Cited

U.S. PATENT DOCUMENTS

| 2011/0144760 A1 | 6/2011 | Wong et al. |
| 2016/0256279 A1 | 9/2016 | Sanders et al. |
| 2017/0172747 A1 | 6/2017 | Bake et al. |

FOREIGN PATENT DOCUMENTS

| JP | 2011172920 A | 9/2011 |
| WO | WO 2016/012730 A1 | 1/2016 |

OTHER PUBLICATIONS

International Search Report related to Application No. PCT/FR2018/053117 dated Mar. 25, 2019.
Japanese Office Action dated Oct. 4, 2022.

*Primary Examiner* — Mohammad Ali
*Assistant Examiner* — Saad M Kabir
(74) *Attorney, Agent, or Firm* — von Briesen & Roper, s.c.

(57) ABSTRACT

A method for producing a tailor-made implant intended to be implanted at an implantation site of a damaged bone part, the method comprising a step in which a 3D representation of a standard implant is superposed on a 3D representation of a damaged bone part by positioning said standard implant on an implantation site of the damaged bone part, in order, if necessary, to modify the dimensions and/or to adjust the shape of said standard implant, and also, if necessary, to modify the outer surface of said standard implant, which may be either the impression or substantially the impression of the outer surface of said bone part in the state prior to superpositioning of said implant, when the geometry of the damaged bone part is intended to be retained, or a functional outer surface, when said tailor-made implant is intended to be used at the interface of two bone parts cooperating with each other.

11 Claims, 7 Drawing Sheets

(51) Int. Cl.
  *B33Y 80/00* (2015.01)
  *B29C 64/386* (2017.01)
  *G05B 19/4099* (2006.01)
  *B29L 31/00* (2006.01)
  *G06T 7/00* (2017.01)

(52) U.S. Cl.
  CPC .......... *B33Y 80/00* (2014.12); *G05B 19/4099* (2013.01); *A61F 2002/30948* (2013.01); *A61F 2002/30952* (2013.01); *A61F 2002/30957* (2013.01); *B29L 2031/7532* (2013.01); *G05B 2219/35134* (2013.01); *G06T 7/0012* (2013.01); *G06T 2207/30008* (2013.01)

(58) Field of Classification Search
  CPC ...... A61F 2/30756; A61F 2/38; B29C 64/386; B33Y 50/00; B33Y 80/00; G05B 19/4099; G05B 2219/35134; B29L 2031/7532; G06T 7/0012; G06T 2207/30008; A61B 2034/104; A61B 2034/105; A61B 2034/108; A61B 34/10
  USPC .......................................................... 700/98
  See application file for complete search history.

METHOD FOR PRODUCING A TAILOR-MADE IMPLANT

CROSS-REFERENCE TO RELATED APPLICATION

This Application is a 35 USC § 371 US National Stage filing of International Application No. PCT/FR2018/053117 filed on Dec. 5, 2018 and claims priority under the Paris Convention to French Patent Application No. 17 61629 filed on Dec. 5, 2017.

FIELD OF THE DISCLOSURE

The present invention relates to a method for producing a tailor-made implant, a computer program having instructions for executing the method for producing said tailor-made implant, a recording medium storing said computer program, a recording medium on which said computer program is stored, and an installation for producing a tailor-made implant.

BACKGROUND OF THE DISCLOSURE

A joint is composed mainly of:
cartilage, neither innervated nor vascularized, resisting poorly to wear;
synovial tissue, which is richly vascularized and which nourishes the cartilage and lubricates the joint;
ligaments, tendons and muscles for supporting the joint.
Osteoarticular diseases account for about 10% of all the pathologies identified in France each year [Bulletin d'information en économie de la sante no. 111 (2006)]. These inflammatory and degenerative diseases of the joints are mostly the result of ageing or trauma. They gradually cause wear of the cartilage, which results in severe physical impairment. At present, there is not really any treatment available for repairing the cartilaginous tissue, except for the implantation of an articular implant (arthroplasty) for restoring mobility to the joint, arthrodesis for immobilizing the joint, and osteotomy for adjusting the orientation of the mechanical axis.

For example, one of these pathologies is osteoarthritis, the most common disease of the joints. Osteoarthritis is a public health problem with a steadily increasing prevalence: 15% in 1990 to 18% expected in 2020.

Osteoarthritis causes significant functional limitation and a reduced quality of life and has a significant psychological impact. In osteoarthritis, there is a deterioration not only of the cartilage, but also of all the articular components (the bone, the synovial tissue, the tendons, and the muscles).

The knees, hips and lumbar spine are the first to be affected by this degenerative process, since these are the joint regions most exposed to the weight of the body and to excess weight. The fingers, cervical spine and shoulder also undergo this degenerative process, this time linked to the repetitive hypermobility of the joint. However, this pathology can affect any joint. Mention may also be made of the degenerative processes affecting the locomotor system.

Other pathologies may be mentioned, such as arthritis, rheumatoid arthritis, lumbago, osteoporosis and musculoskeletal disorders.

One of the treatments for these pathologies of the joints is to replace the damaged joint surfaces with implants. According to current techniques, the implants used in this case necessitate substantial resection of the articular surfaces, this resection resulting either in the formation of a plane surface at the end of the bone concerned, or in the formation of several plane surfaces angled with respect to one another and constituting an approximation of the actual joint surface.

For it to be fitted in place, this type of prosthetic element requires substantial resection of the bone. This resection in turn requires the use of complex surgical equipment in order to precisely define the plane or planes of the resection surface that is to be formed. In addition, since the resection surface is plane or composed of several plane portions, it is necessary to provide very strong and deep anchoring of the prosthetic element in the part of the bone associated with the articular surface, so as to ensure the rigid attachment of the prosthesis. However, anchoring elements such as screws, pins, studs, etc., require the drilling of substantial anchoring holes in the bone that is to be treated. This substantial drilling or piercing in turn requires the use of specific tools. In addition, the degree of drilling or piercing of the bone can lead to damaging consequences for the part of the bone that has undergone this perforating, particularly as regards its mechanical strength when stresses are applied to the bones constituting this joint during movements since, on account of its length, the anchoring element transmits the stress to a zone of the bone that is not designed to support this stress.

Moreover, in the case of an extensive and substantially plane resection, the support of the prosthesis on the resection surface is unsatisfactory, since this surface is essentially composed of spongy bone, support on the cortical periphery of the bone being insufficient as regards transmission the force.

Finally, the known implants do not allow practitioners to choose from a sufficient range in order to meet the degrees of articular freedom chosen, said implants being standardized.

There is therefore a need for an implant production method which makes it possible to obtain a tailor-made implant, respects the anatomical structures and also the complex shapes of the joints of each individual, and thus allows the implant to be adapted to the morphology and/or pathology of the individual.

SUMMARY OF THE DISCLOSURE

The present invention aims to remedy the disadvantages of the prior art and to overcome the above constraints by proposing a method for producing a tailor-made implant.

Indeed, the present invention relates to a method for producing a tailor-made implant intended to be implanted on a placement site of a damaged bone part, the method comprising a step of fading-based superpositioning of a 3D representation of a standard implant on a 3D representation of a damaged bone part by positioning said standard implant on a placement site of the damaged bone part, in order if necessary to make modifications to the dimensions and/or adjust the shape of said standard implant, and optionally also to modify the outer surface of said standard implant, which can be either the impression or substantially the impression of the outer surface of said bone part in the state before superpositioning of said implant when the geometry of the damaged bone part is intended to be preserved, or a functional outer surface, when said tailor-made implant is intended to be used at the interface of two bone parts cooperating with each other.

The present invention also relates to a method for producing a tailor-made implant intended to be implanted on a placement site of a damaged bone part, the method comprising a step according to which a local modification has been directly performed on a placement site of the graphical 3D representation of said damaged bone part, the shape and the dimensions of the anchoring surface of the implant depending on the shape and dimensions of said at least one local modification in order to permit the anchoring of said implant on said bone portion to be treated, the outer surface subsequently being determined.

Thus, and advantageously, the anchoring surface of said tailor-made implant obtained by the method according to the invention is not plane and conforms to the placement site at the surface of said damaged bone part, either by modifying the dimensions and/or adjusting the shape of a standard implant taking into account at least one parameter of the damaged bone part, or by determining the shapes and dimensions of said anchoring surface with respect to the shapes and dimensions of said at least one local modification performed on the graphical representation of the damaged bone part.

The damaged bone surface is therefore advantageously preserved. The method according to the invention makes it possible to avoid substantial and unnecessary resection of the bone and to determine only the necessary resections, which is in contrast to the previous techniques, typically with cutting by sawing, according to which the anchoring of the implant is of the plane-to-plane type.

We note that it is clear from the subject matter of the invention that the determination of the tailor-made implant is obtained from the one or more images acquired during a preliminary step (step i) and that no action is performed at any time on the body of the patient.

Thus, the anchoring surface of the tailor-made implant produced by the method according to the invention takes the exact place of the recessed bone structures, ensuring a healthy distribution of the stresses and a primary immobilization of the implant without micromovements, and thus ensuring lasting fixation and bone reconstruction.

Advantageously too, the method according to the invention makes it possible to determine the outer surface of the tailor-made implant, this outer surface being either the impression or substantially the impression of the outer surface of said bone part when the geometry of the damaged bone part is intended to be preserved, or a functional surface, when said tailor-made implant is intended to be used at the interface of two bones parts cooperating with each other.

Thus, and in one case, the method for producing the tailor-made implant permits the reconstruction of the outer surface of the damaged bone part, and in another case, the outer surface is a functional surface determined according to the conjugate surface of another bone part with which said bone part to be repaired cooperates so as to restore mobility to the joint in the context of arthroplasty, or to immobilize the joint in the context of arthrodesis, or to reorient the mechanical axis in the context of osteotomy, in order to obtain a tailor-made implant which permits anatomical correction of a pathology and which is adapted to the physical and mechanical properties of the bone surfaces.

The method according to the invention therefore offers a choice of tailor-made implants responding to the degrees of joint freedom and adapted to each morphology and pathology.

The method according to the invention also saves time in the operating theater, reduces costs and also spares bone substance.

Thus, the invention relates to a method for producing a tailor-made implant intended to be implanted on a placement site of a damaged bone part, characterized in that it comprises the following steps:

i. acquisition of one or more images of at least said damaged bone part;
ii. graphical 3D representation of the image of at least said damaged bone part acquired at step i.;
iii. a) fading-based superpositioning of a 3D representation of a standard implant on the 3D representation obtained at step ii., by positioning said standard implant on a placement site at the surface of said damaged bone part, then, if necessary, modification of the dimensions and/or adjustment of the shape of said standard implant, taking account of at least one parameter of the damaged bone part, then optional modification of the outer surface of said standard implant, the modification of the outer surface of said standard implant being such that said standard implant thus positioned on said placement site is imparted an outer surface which is:
   the impression or substantially the impression of the outer surface of said bone part, occupied by said standard implant, in the state prior to superpositioning of said implant, when the geometry of said bone part is intended to be preserved, or
   a functional outer surface, when said tailor-made implant is intended to be used at the interface of two bone parts cooperating with each other, said functional surface being determined in such a way that, being at least partially in contact with a conjugate surface of the other bone part with which said damaged bone part cooperates, it ensures the articulation of said bone parts,
or
   b) having performed at least one local modification directly on a placement site of the graphical 3D representation of said damaged bone part, determination of the shape and dimensions of said anchoring surface of an implant depending on the shape and the dimensions of said at least one local modification performed on said graphical 3D representation, said anchoring surface permitting the anchoring thereof on said damaged bone part to be treated, then determination of the outer surface of said implant;
iv. realization of the tailor-made implant from the definitive parameters of said implant obtained at step iii.

Within the context of the present invention, "placement site" is understood as meaning at least one zone of the bone part that will be removed so as to receive the implant.

The placement site can be local or over the whole surface of the bone part. The placement site can be unicompartmental, bicompartmental or tricompartmental. Thus, the placement site corresponds to the possible configurations of the recovery of the bone surface. Typically, the bone recovery can range from 10 to 100% bone recovery.

Typically, the bone recovery can be total (100% bone recovery), and the totality of the bone part is restored.

Thus, the tailor-made implant can be a unicompartmental, bicompartmental or tricompartmental implant.

Purely by way of illustration, an implant will be able to be regarded as unicompartmental in the context of bone recovery of up to about 30% of the bone part, as bicompartmental in the context of bone recovery of between about 30% and 60% of the bone part, and as tricompartmental in the context of bone recovery of between about 60% and 100% of the bone part.

Within the context of the present invention, "bone part" is understood as meaning the end of a bone or the outer surface of part of a bone.

Typically, the bone parts will be able to be chosen from the bones composing the knee, such as the tibia and the femur, the lumbar and cervical vertebrae, the acromion of the scapula, the head of the humerus, the clavicle, the bones composing the foot, the bones composing the ankle, the bones composing the pelvis, the bones composing the hip, the lumbar spine, the cervical spine, the bones composing the shoulder, the bones composing the elbow, the bones composing the wrist, the bones composing the hand, and the teeth.

In a preferred embodiment of the invention, the bone parts cooperate with each other and form a joint.

Purely by way of illustration, mention will be made of the intervertebral joints, the lumbosacral joint, the sacrococcygeal joint, the intercoccygeal joints, the sacroiliac joints, the symphysis pubis, the glenohumeral joint, the acromioclavicular joint, the humero-ulnar joint, the humeroradial joint, the proximal radio-ulnar joint, the radiocarpal joint, the distal radio-ulnar joint, the joints between the carpal bones, the carpometacarpal joints, the intermetacarpal joints, the metacarpophalangeal joints, the interphalangeal joints, the hip joint, the tibiofemoral joint, the patellofemoral joint, the proximal tibiofibular joint, the ankle joint, the distal tibiofibular joint, the joints between the tarsal bones, the tarsometatarsal joints, the intermetatarsal joints, the metatarsophalangeal joints, the interphalangeal joints.

Preferably, the two parts cooperating with each other will be the tibia and the femur, preferably the distal end of the femur and the proximal end of the tibia.

A "damaged bone part" is understood as meaning any bone part that has suffered trauma, deterioration, degeneration, inflammation, disorganization of the bone tissue, or a degenerative process.

Typically, the parameters of the damaged bone part will be able to be chosen from the densitometric properties, such as porosity and density, the mechanical properties, such as its elastic properties and its viscoelastic properties.

The "outer surface" of the implant is understood as meaning the part of the implant that is not intended to be contact directly with the bone surface receiving the implant.

The "functional outer surface" is understood as meaning the part of the implant that is not intended to be in contact with the bone surface receiving the implant and that is intended to be used at the interface of two bone parts cooperating with each other, for example so as to create the frictional torque.

The functional outer surface is a functional surface which represents a surface of the implant that will cooperate with another functional surface of another bone part in order to create the frictional torque. The functional surface thus represents a friction surface which gives functionality to the joint formed by a healthy bone part and a damaged bone part.

Generally, the joints comprise one or more functional surfaces which provide the mobility and the morphology particular to the individual. The shape and the number of these surfaces thus vary according to the ability of the joint to meet different degrees of functional mobility.

In the prior art, the implants obtained do not meet the specific nature of the functional surfaces of the implant in accordance with the joint, hence the specific nature of the mobility and the morphology of each individual. For this reason, taking the example of a knee joint, the standard implants have certain troublesome consequences for the patient: dislocation of the tibia, cutting of the tibial slope, and change of the mobility and stability of the joint.

The method of the present invention makes it possible to overcome these drawbacks by making available an implant with functional surfaces which correspond to those of the damaged bone part in such a way as to preserve or restore the mobility and the morphology of the individual before the implant is fitted in place.

The method of the present invention proposes extracting not only the anchoring surface but also the functional surface of the tailor-made implant from the fading-based superpositioning of a 3D representation of a standard implant on the obtained 3D representation of the damaged bone part. More precisely, this extraction has been performed when the damaged bone part was in a functional position with the other bone part.

In the event that the state of the damaged bone part does not permit extraction of the one or more functional surfaces of the implant, the method comprises a step in which a negative 3D image is taken from the other bone part conjugate to the damaged bone part, in order to extract the one or more functional surfaces, taking account of the mobility of the individual.

Thus, the method of the present invention, in which the functional surfaces of the implant are determined, makes it possible to reproduce the frictional torque between two bone parts of the joint and permits:
    preservation of the integrity of the morphology;
    preservation of the frictional torque, and therefore the mobility
    intra-articular and extra-articular preservation of the ligaments and menisci, which permits preservation of the mobility and stability of the individual.

Within the context of the present invention, the term "anchoring surface" is understood as meaning the surface of the implant that is intended to be directly in contact with the bone part (placement site) receiving the implant.

Within the context of the present invention, the term "conjugate surface" is understood as meaning a surface which for example may correspond, without limitation, to the outer surface of another implant received at the surface of a second bone part or corresponding to the surface of a second bone part cooperating with the first bone part receiving the implant.

Thus, and according to one embodiment, the method for producing a tailor-made implant intended to be implanted on a placement site of a damaged bone part according to the invention comprises the following steps:
  i. acquisition of one or more images of at least said damaged bone part;
  ii. graphical 3D representation of the image of at least said damaged bone part acquired at step i.;
  iii. superpositioning of a 3D representation of a standard implant on the 3D representation obtained at step ii., by positioning said standard implant on a placement site at the surface of said damaged bone part, then, if necessary, modification of the dimensions and/or adjustment of the shape of said standard implant, taking account of at least one parameter of the damaged bone part, then modification of the outer surface of said standard implant, the modification of the outer surface of said standard implant being such that said standard implant thus positioned on said placement site is imparted an outer surface which is the impression or substantially the impression of the outer surface of said bone part, occupied by said standard implant, in the state prior to superpositioning of said implant, when the geometry of said bone part is intended to be preserved;
  iv. realization of the tailor-made implant from the definitive parameters of said implant obtained at step iii.

The 3D representation of the implant will be superposed on the 3D representation of the bone part at the surface of which said implant is intended to be received and will make it possible to dissociate the bone part to be preserved and the bone part to be eliminated in order to replace it with the implant, this being in order to determine the limitations of the implant and also the limitations of the anchoring in the bone.

Advantageously, and according to one embodiment, the implant is the correct and personalized representation of the bone part, allowing the bone surface to be reconstructed identically to the state it was in before being damaged. This superpositioning will therefore allow perfect recovery of said bone part, with the possibility of modification such that the tailor-made implant thus obtained ensures an anatomical correction of a pathology.

In another embodiment, the method for producing a tailor-made implant intended to be implanted on a placement site of a damaged bone part according to the invention comprises the following steps:
  i. acquisition of one or more images of at least said damaged bone part;
  ii. graphical 3D representation of the image of at least said damaged bone part acquired at step i.;
  iii. superpositioning of a 3D representation of a standard implant on the 3D representation obtained at step ii., by positioning said standard implant on a placement site at the surface of said damaged bone part, then, if necessary, modification of the dimensions and/or adjustment of the shape of said standard implant, taking account of at least one parameter of the damaged bone part, then optional modification of the outer surface of said standard implant, the modification of the outer surface of said standard implant being such that said standard implant thus positioned on said placement site is imparted an outer surface which is a functional outer surface, when said tailor-made implant is intended to be used at the interface of two bone parts cooperating with each other, said functional surface being determined in such a way that, being at least partially in contact with a conjugate surface of the other bone part with which said damaged bone part cooperates, it ensures the articulation of said bone parts;
  iv. realization of the tailor-made implant from the definitive parameters of said implant obtained at step iii.

The 3D representation of the implant will be superposed on the 3D representation of the bone part at the surface of which said implant is intended to be received and will make it possible to dissociate the bone part to be preserved and the bone part to be eliminated in order to replace it with the implant, this being in order to determine the limitations of the implant and also the limitations of the anchoring in the bone.

Advantageously again, the outer surface will additionally be reworked in order to obtain a functional bone surface, in such a way as to recreate the complementarity of the joint.

Typically, the implant will be able to be a standard implant, an implant blank or a new embodiment corresponding to a new standard.

Typically, the implant will be able to be selected from a standard library of 3D implant representations, adapted to the morphology of the patient and the degrees of repair to be performed.

The implant will be able to assume any geometric shape (cylindrical, parallelepipedal, cuboid, etc.) or any random and non-geometric shape. Alternatively, the implant will be able to be made freehand.

In yet another embodiment, the method for producing a tailor-made implant intended to be implanted on a placement site of a damaged bone part according to the invention comprises the following steps:
  i. acquisition of one or more images of at least said damaged bone part;
  ii. graphical 3D representation of the image of at least said damaged bone part acquired at step i.;
  iii. having performed at least one local modification directly on a placement site of the graphical 3D representation of said bone part to be treated, determination of the shape and dimensions of said anchoring surface of an implant depending on the shape and the dimensions of said at least one local modification performed on said graphical 3D representation, said anchoring surface permitting the anchoring thereof on said damaged bone part, then determination of the outer surface of said implant;
  iv. realization of the tailor-made implant from the definitive parameters of said implant obtained at step iii.

Advantageously, and in this embodiment, the shapes and dimensions of the anchoring surface of said implant are determined according to the shape and dimensions of at least one local modification made directly on the graphical representation of said bone part intended to receive said implant.

Indeed, from the realization of at least one local modification made on the graphical representation of said bone part intended to receive the implant, the shape and dimensions of the implant will be determined in such a way that the anchoring surface of said implant is the impression or substantially the impression of the local modification projected on said bone part.

The complementarity of the anchoring zone of the implant to the local modification of the bone part makes it possible to limit the bone resections and thus preserve the anatomical structures.

Advantageously, the shapes and dimensions of the anchoring surface of the implant perfectly correspond to the shapes and dimensions of said at least one local modification made on the bone part. Thus, the periphery of the local modification corresponds to the periphery of the anchoring surface of the implant.

The quality of the images obtained will dictate the quality of the tailor-made implant and its precision. The method according to the present invention comprises a step of acquisition of one or more images by computed tomography (CT) and/or magnetic resonance imaging (MRI) of at least one bone part, or any other method of acquisition of one or more images.

Computed tomography has better spatial resolution, and the acquisition of the images of the bone parts is more precise. In a preferred embodiment, magnetic resonance imaging (MRI) will be used to visualize the cartilage with precision. In another embodiment, the image acquisition is effected by the combination of computed tomography and magnetic resonance imaging, or by any other method permitting the acquisition of images or 3D representations.

Advantageously, the production method according to the invention makes it possible to produce a tailor-made implant according to the modifications and/or intervention to be made on at least one bone part of the patient and is therefore adapted and customized for each patient.

Indeed, the acquisition step gives rise to the layer-by-layer representation of the state and the exact form of said at least one bone part. The 2D images acquired will then be transformed to 3D at step ii. This results in a 3D volume file that is an exact and unique representation of the patient's morphology and in particular of the damaged bone part.

Said images thus acquired will subsequently be modeled in 3D on a computer.

Purely by way of illustration, the 3D support formats will be STEP, IGES, NURBS, etc. The transmission of said images is done by encoding. We mention, for example, the DICOM files from SCAN.

The images will be transformed to a 3D CAD file.

In various particular embodiments of the implant production method, each having its particular advantages and capable of many possible technical combinations:

The superpositioning of a 3D representation of a standard implant on the 3D representation obtained at step ii. is performed by fading.

At step iii. b), the outer surface of said implant is plane and rounded, or is the impression or substantially the impression of the zone of said bone part to be treated, in the state before its removal by said at least one local modification, or again when said tailor-made implant is intended to be used at the interface of two bones parts cooperating with each other, said outer surface of said implant being a functional outer surface determined in such a way that, being at least partially in contact with a conjugate surface of the other bone part with which said damaged bone part cooperates, it ensures the articulation of said bone parts.

Advantageously, this embodiment makes it possible to rework the complementarity of the joint.

At step iii. a), the determination of said functional surface is performed while the two bone parts are in the functional position in the graphical 3D representation, one or more images of said two bone parts having been acquired at step i).

The term "functional position" is understood as the position in which the two bone parts are not dislocated or displaced from their functional seat. It therefore corresponds to the ideal functional position for the patient according to his morphology and his mobility.

The functional surfaces extracted make it possible to produce a tailor-made implant able to reproduce the different degrees of mobility of the joint in question which are particular to the individual. This specificity of the functional mobility is not reproduced in the standard implants.

Said implant is a part of a medical device intended to be implanted.

In a preferred embodiment, said conjugate surface corresponds to the outer surface of another implant received at the surface of said other bone part cooperating with said damaged bone part.

The outer surface of said implant is determined by removal of material from a solid surface of the graphical representation of the implant.

At step iii. a), the portion of the implant to be removed is determined by subtracting the only graphical representation of said at least one damaged bone part obtained at step ii. from the graphical representation representing the assembly composed of bone part and standard implant positioned on its placement site.

The outer surface of said implant is determined by addition of material.

Typically, and at step iii. b), said local modification will be able to be chosen from arthroplasty, osteotomy or arthrodesis.

Arthrodesis is understood as the intervention intended to fix a joint by bone fusion and to block it by osteosynthesis.

Arthroplasty is the surgical intervention for restoring the mobility of a joint by creating a new articular space.

Osteotomy is understood as the surgical procedure consisting of cutting the diaphysis of a long bone in order to better reorient an axis or several axes of said bone, so as to better reposition the joints lying above and below.

In a preferred embodiment, the local modification is an arthroplasty, preferably the formation of a continuous recess on at least a part of the bone surface.

At step iv), said implant is produced by additive manufacturing.

The additive manufacturing is chosen from the techniques of stereolithography, selective laser sintering (SLS), fused deposition modeling (FDM), selective laser melting (SLM), or any method of additive manufacturing such as electron beam melting (EBM).

The manufacturing will also be able to be performed by conventional tools, such as 5-axis machining for example.

In a preferred embodiment, the implant is made of a biocompatible material.

Biocompatible material is understood as any material having the capacity not to interfere with and not to degrade the biological environment in which it is used.

Examples that may be mentioned purely by way of illustration are metals and metal alloys such as stainless steels, particularly 316L stainless steel or 17-4PH stainless steel, titanium and titanium alloys such as titanium grade 1, grade 2, grade 4, grade 5, grade 23, chromium-cobalt, ceramics such as alumina and zirconia. Mention will also be made of polyethylene or ultra-high density polyethylene, polyamide 12 (PA12) and polyetheretherketone (PEEK).

Preferably, the material will be chosen from alumina ceramic, chromium-cobalt, polyetheretherketone.

In another embodiment, the implant will be made of a biocompatible and resorbable material.

Purely by way of illustration, the material will be able to be chosen from magnesium, resorbable polymers, such as polylactides (PLA), polyglycolides (PGA), polyhydroxybutyrates (PHB) or polyhydroxyvalerates (PHV), but most often of suitable copolymers such as polylactides (L-D/L).

The method comprises a supplementary step of additive manufacturing of said at least one bone part acquired at step ii.

The additive manufacturing of said at least one bone part makes it possible to verify the suitability of the implant produced by the method according to the invention.

The invention also relates to a computer program having instructions for executing the method for producing a tailor-made implant according to the invention, when the program is executed by a processor.

The invention also relates to a recording medium on which the computer program according to the invention is stored.

The invention also relates to an installation for producing a tailor-made implant, comprising first image-acquisition means and second calculation means configured to execute the method for producing a tailor-made implant by the method according to the invention.

The installation further comprises a three-dimensional printer configured to form a three-dimensional implant.

The first image-acquisition means comprise a magnetic resonance imaging device and/or a computed tomography imaging device.

The invention also relates to a tailor-made implant obtained by the method according to the present invention.

In a preferred embodiment, the implant is intended to be anchored on at least two bones parts cooperating with each other, after at least one local modification of at least one of said bone parts, preferably of both bone parts.

Preferably, the at least two bone parts correspond to a zone of juxtaposition defining a joint.

Purely by way of illustration, mention will be made of the intervertebral joints, the lumbosacral joint, the sacrococcygeal joint, the intercoccygeal joints, the sacroiliac joints, the symphysis pubis, the glenohumeral joint, the acromioclavicular joint, the humero-ulnar joint, the humeroradial joint, the proximal radio-ulnar joint, the radiocarpal joint, the distal radio-ulnar joint, the joints between the carpal bones, the carpometacarpal joints, the intermetacarpal joints, the metacarpophalangeal joints, the interphalangeal joints, the hip joint, the tibiofemoral joint, the patellofemoral joint, the proximal tibiofibular joint, the ankle joint, the distal tibiofibular joint, the joints between the tarsal bones, the tarsometatarsal joints, the intermetatarsal joints, the metatarsophalangeal joints, the interphalangeal joints.

In a preferred embodiment, the implant is intended to be anchored on the proximal end of the tibia and the distal end of the femur of the tibiofemoral joint.

The present invention also relates to an implant, said implant comprising:
an anchoring surface, said surface being the impression or substantially the impression of:
a placement site of a damaged bone part;
at least one local modification on a damaged bone part;
an outer surface, said outer surface being:
the impression or substantially the impression of the outer surface of said bone part, occupied by said standard implant, in the state before superpositioning of said implant, when the geometry of said bone part is intended to be preserved, or
a functional outer surface, when said tailor-made implant is intended to be used at the interface of two bones parts cooperating with each other, said functional surface being determined in such a way that, being at least partially in contact with a conjugate surface of the other bone part with which said damaged bone part cooperates, it ensures the articulation of said bone parts;
at least one anchoring device intended to cooperate with at least one anchoring zone on at least one part of the bone part.

In one embodiment of the invention, the anchoring device is a protuberance.

In another embodiment, the part providing the anchoring can be a hook.

The anchoring surface of the implant according to the present invention comprises a surface relief for reinforcing the anchoring of said implant on the bone surface.

Typically, and purely by way of illustration, this surface relief is formed by projections and/or hollows, and/or trabeculae.

For example, these projections are ribs or pins, and the hollows are tubes formed within the thickness of the inner face of the implant.

These projections and/or these hollows can be aligned by being spaced regularly, or irregularly, from each other in order to define radially or substantially radially radiating lines or branches.

Thus, and advantageously, the surface relief of the inner face makes it possible to reinforce the anchoring of the implant on the bone surface and makes it possible to promote ossification after the implant has been put in place.

Said implant is made of alumina ceramic.

In another embodiment, and purely by way of illustration, the implant can be made of a biocompatible material, that is to say a material having the ability not to interfere and not to degrade the biological environment in which it is used.

Examples that may be mentioned are metals and metal alloys such as stainless steels, particularly 316L stainless steel or 17-4PH stainless steel, titanium and titanium alloys such as titanium grade 1, grade 2, grade 4, grade 5, grade 23, chromium-cobalt, ceramics such as alumina and zirconia, tantalum, complex alloys such as a an alloy of titanium with aluminum or an alloy of titanium with tantalum, and all alloys possible with additive manufacturing. Mention will also be made of polyethylene or ultra-high density polyethylene.

Said at least one local modification is an arthroplasty defining a recess intended to receive said implant, the anchoring surface of said implant being the impression of the zone of the bone surface in the state before its removal by recessing.

Indeed, in a preferred embodiment, the local modification is an arthroplasty and consists in resecting at least one bone surface in order to determine a recess, said recess being adapted to receive an implant according to the invention.

The implant comprises at least two tabs, said at least two tabs being connected by said anchoring device.

In one embodiment, the implant or prosthesis has a shape chosen from a U-shape, a V-shape, a W-shape, an X-shape and an O-shape and will be a customized implant depending on the pathology and/or morphology of the patient.

In a preferred embodiment, the implant according to the present invention is a U-shaped implant comprising two tabs, said two tabs being connected by the anchoring device.

In another embodiment, the implant is a one-piece implant, the implant is an implant composed of two coupled implants, the implant is composed of different implants, screws, plates, rods that combine.

The invention also relates to an implant within the meaning of the present invention for its use in the treatment of osteoarticular pathologies such as osteoarthritis, arthritis, rheumatoid arthritis, lumbago, osteoporosis, musculoskeletal disorders, etc.

Preferably, the implant according to the invention is used in the treatment of osteoarthritis of the knee.

BRIEF DESCRIPTION OF THE DRAWINGS

Other advantages, aims and particular features of the present invention will become clear from the following description which is given for explanatory purposes and is non-limiting and in which reference is made to the appended drawings, in which.

DETAILED DESCRIPTION OF THE DISCLOSURE

First of all, it will be noted that the figures are not to scale.

Figure 1:
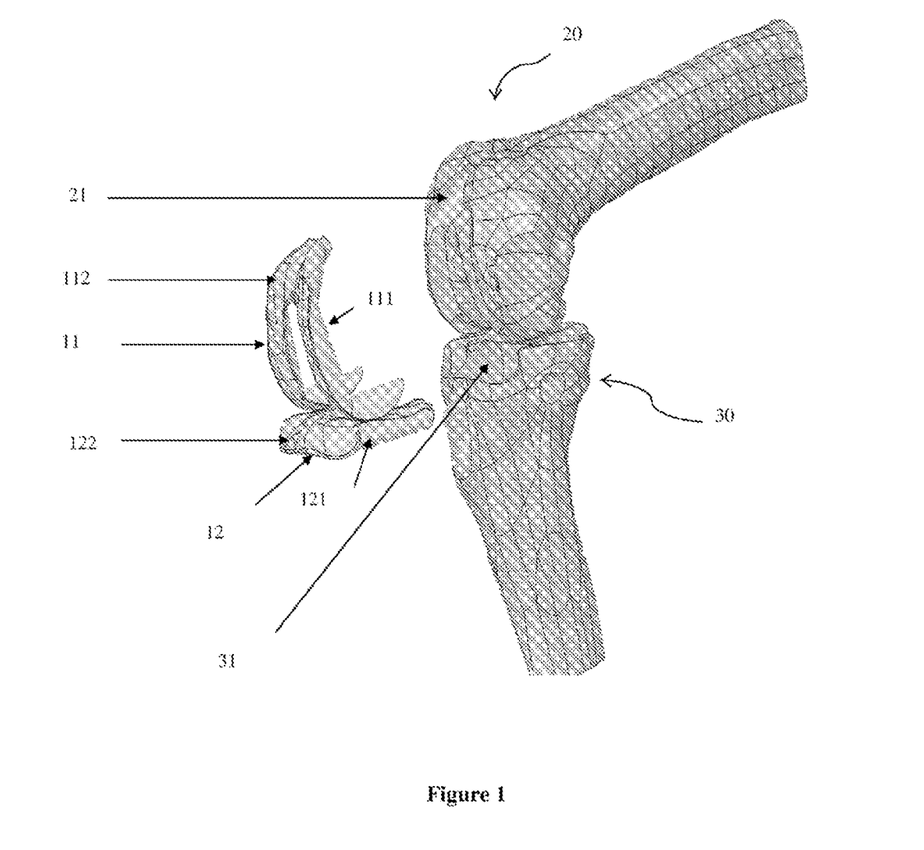
FIG. 1 is a perspective view of two tailor-made implants, produced by the method according to the invention, and of the tibiofemoral joint.

The images of the bone parts, here the bone parts cooperating in the tibiofemoral joint, have been acquired by magnetic resonance imaging and have then been segmented and modeled in 3D on a computer, said images being transmitted in STL format. A 3D image of the tibiofemoral joint, i.e. of the proximal end 30 of the tibia and the distal end 20 of the femur has thus been acquired, and, for example as shown in FIG. 1, in the functional position.

On the basis of this 3D image of the tibiofemoral joint in the functional position, the recesses necessary for receiving the tailor-made implants 11, 12 have been made on the 3D image of the tibiofemoral joint in order to modify locally the proximal tibial bone end 30 and distal femoral bone end 20.

A recess 21 has been formed on the distal femoral end 20 and a recess 31 has been formed on the proximal tibial end 30.

By virtue of each recess 21, 31, the shape and dimensions of each implant, respectively 11 and 12, will be determined in such a way that the anchoring surface 111, 121 of each implant is the impression of the removed zone 21, 31 of the distal femoral end 20 and of the proximal tibial end 30.

The tailor-made implants 11 and 12 are intended to be used at the interface of two bones parts cooperating with each other, the outer surfaces 112 and 122 of the implants 11 and 12 being functional surfaces.

Thus, the functional surface 112 of the implant 11 will be determined according to the conjugate surface of the proximal tibial end 30 with which the distal femoral end 20 cooperates, this to ensure the articulation between the proximal tibial end 30 and the distal femoral end 20, the conjugate surface corresponding to the functional outer surface 122 of the implant 12.

In the same way, the functional surface 122 of the implant 12 will be determined according to the conjugate surface of the distal femoral end 20 with which the proximal tibial end 30 cooperates, this to ensure the articulation between the proximal tibial end 30 and the distal femoral end 20, the conjugate surface corresponding to the functional outer surface 112 of the implant 11.

The articulation between the proximal tibial end 30 and the distal femoral end 20 is advantageously recovered.

Figure 2:
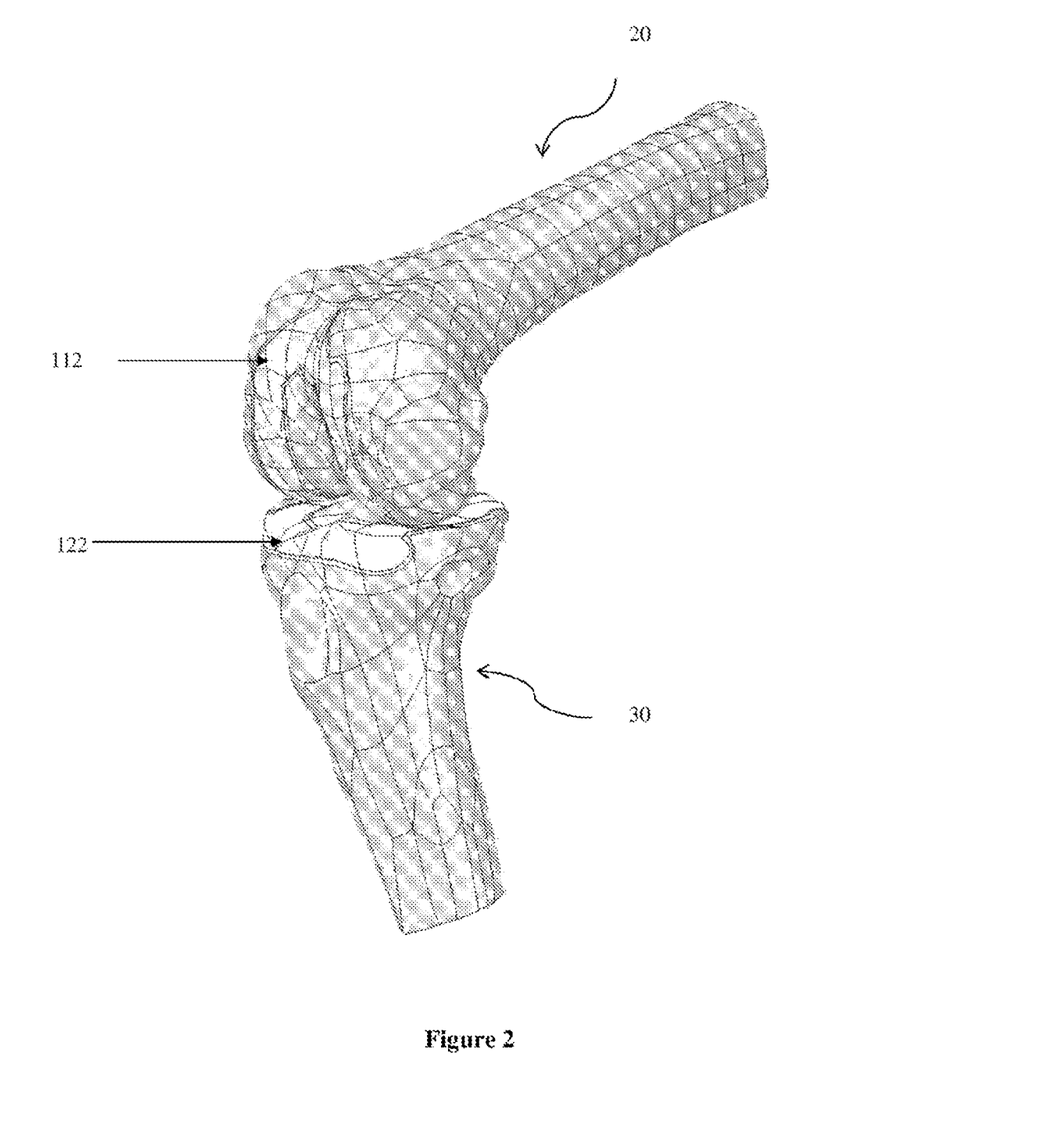
FIG. 2 is a perspective view of two tailor-made implants produced by the method according to the invention, said implants being anchored in the tibio-femoral joint.

Advantageously, the method for producing a tailor-made implant according to the present invention will make it possible to resect the bone only to the extent required and will preserve the bone reserves of the patient and recreate the tibiofemoral joint (FIG. 2).

In the present embodiment, the distal femoral end 20 and the proximal tibial end 30 have been made by additive manufacturing in order to verify the suitability of the implants.

Figure 3:
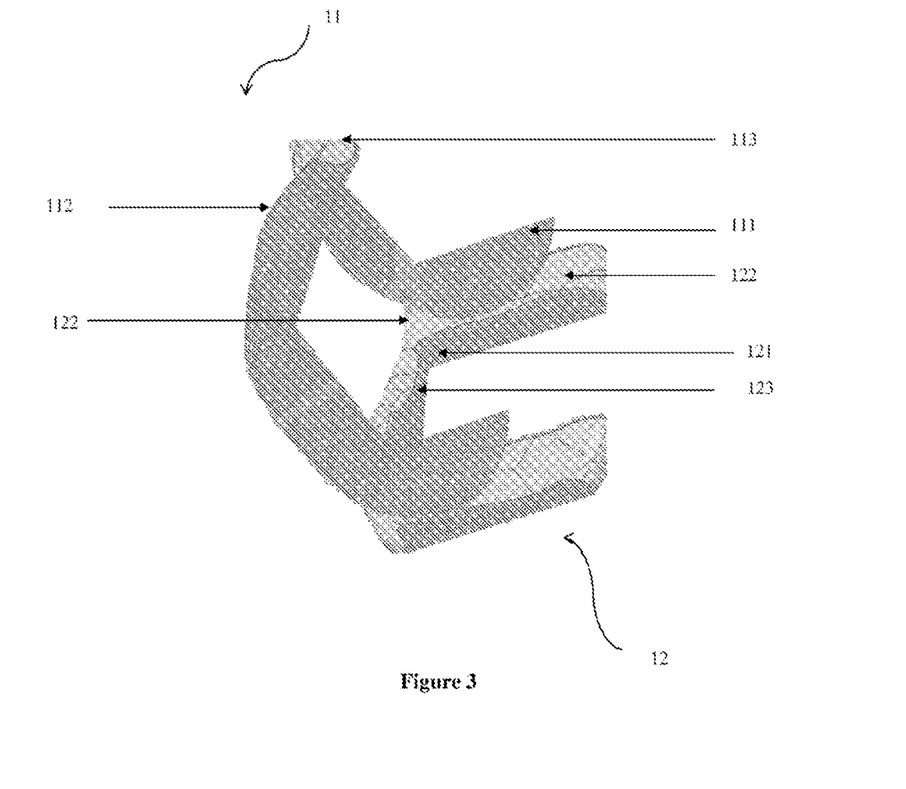
FIG. 3 is a perspective view of two tailor-made implants produced by the method according to the invention.

FIG. 3 shows a tailor-made medical device composed of an implant 11 intended to be received on the distal end 20 of the femur (not shown) and an implant 12 intended to be received on the proximal end 30 of the tibia (not shown), the two implants representing a tricompartmental prosthesis obtained by the method according to the invention.

Each implant comprises an anchoring surface 111, 121 being the impression or substantially the impression of at least one local modification on a damaged bone part, a functional surface 112, 122 intended to be used at the interface of the two bone parts cooperating with each other to ensure the articulation of the tibia and femur, and a protuberance 113, 123 connecting the two tabs of each body. The relationship of the outer surfaces 112 and 122 is the frictional torque.

The anchoring surface of each implant comprises a surface relief intended to reinforce the anchoring of said implant. This inner relief is composed of trabeculae, which are porous structures taking up the design of the spongy bone and permitting particularly effective bone reconstruction.

The implants 11 and 12 are made of titanium. The trabeculae of the anchoring surfaces 111 and 121 of the implants are made by plasma spraying of a titanium oxide suspension.

Advantageously, the implants according to the invention and more particularly the total knee prosthesis according to this particular embodiment of the invention are tailor-made implants, identical to the morphology of the patient and fully integrating the personal functioning of the patient (displacement/sliding/rotation), obtained from the method according to the invention.

Figure 4:
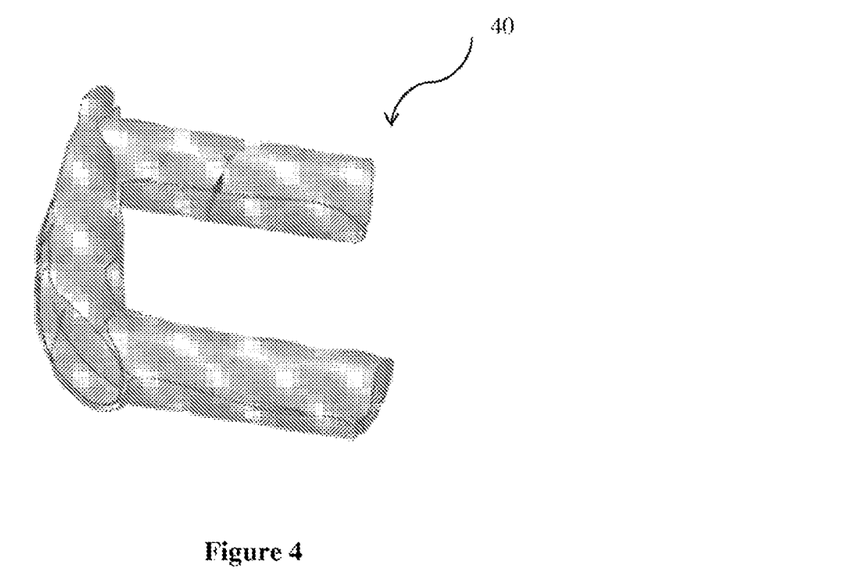
FIG. 4 is a perspective view of a standard implant chosen from a library. The implant is a 60% bicompartmental implant.

FIG. 4 corresponds to the standard implant 40 chosen from a library. The implant is a 60% bicompartmental implant.

The standard implant is modeled in CAD.

Figure 5:
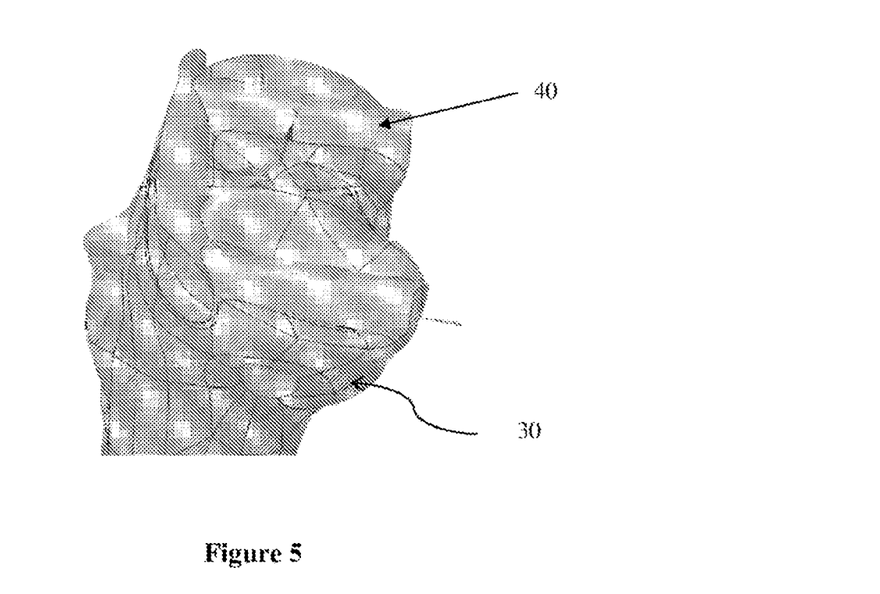
FIG. 5 is a perspective view of a 3D representation of a bone part and the superpositioning of a 3D representation of a standard implant.

FIG. 5 is a perspective view of a 3D representation of a bone part, here the proximal tibial end 30, and the superpositioning of a 3D representation of a standard implant 40.

According to the method for producing a tailor-made implant according to the invention, intended to be implanted on a placement site of a damaged bone part, the images of the proximal end 30 of the tibia have been acquired by magnetic resonance imaging and have been subsequently segmented and modeled in 3D on a computer, said images being transmitted in STL format. A 3D image of the proximal tibial end 30 is thus acquired.

The 3D representation of a standard implant 40 has been superposed on the 3D representation of the proximal end 30 of the tibia, by positioning said standard implant 40 on a placement site at the surface of the damaged proximal end 30 of the tibia.

Figure 6A:
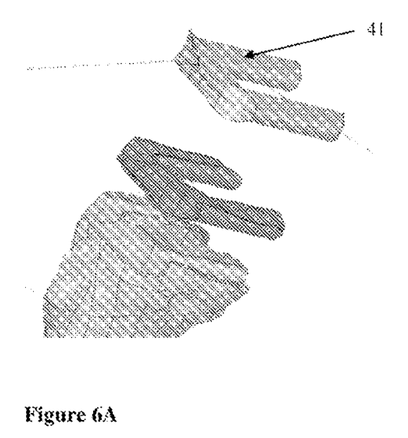
FIGS. 6A AND 6B are perspective views of a 3D representation of a bone part in 3D and of a 3D representation of a standard implant and the modification of the dimensions and/or adjustment of the shape of the 3D representation of said standard implant, and the modification of the outer surface.
Figure 6B:
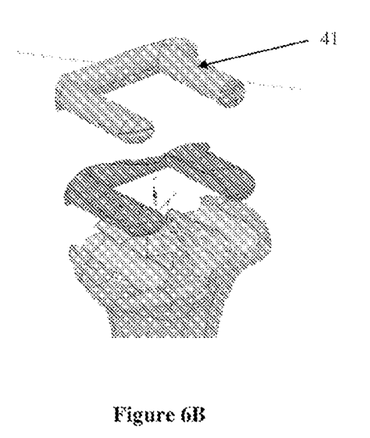

According to FIG. 6, the dimensions of the standard implant 40 will be modified, and the shape of said standard implant 40 will be adjusted by subtracting material from the implant.

The outer surface 41 of said standard implant will be modified in such a way as to be the impression or substantially the impression of the outer surface of said bone part, occupied by said standard implant, in the state before superpositioning of said implant, so as to preserve the geometry of the bone part.

Thus, and advantageously, the geometry of the proximal end will be able to be recreated.

Figure 7:
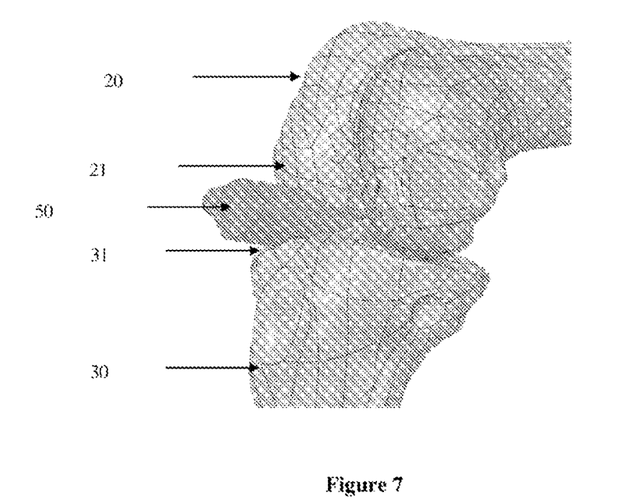
FIG. 7 is a perspective view of a 3D representation of the tibiofemoral joint and a 3D representation of a standard implant specifically designed for the damaged bone parts.

FIG. 7 is a perspective view of a 3D representation of the tibiofemoral joint and of a 3D representation of a standard implant designed specifically for the damaged bone parts.

In the same way as before, the images of the proximal end 30 of the tibia and the distal end 20 of the femur have been acquired by magnetic resonance imaging and have been subsequently segmented and modeled in 3D on a computer, said images being transmitted in STL format. A 3D image of the proximal end 30 of the tibia and of the distal end 20 of the femur is thus acquired.

The 3D representation of an implant 50 designed in a geometrical shape specifically intended for the damaged bone part, that is to say the lateral condyle 21 of the distal end of the femur and the lateral plateau 31 of the proximal end of the tibia, has been superposed on the 3D representation on a placement site at the surface of each damaged bone part, that is to say at the surface of the lateral condyle 21 of the distal end of the femur and at the surface of the lateral plateau of the proximal end of the tibia.

In this case, the 3D representation of the implant does not correspond to a standard implant, but to a 3D representation of a newly created implant determined by the practitioner as being more adapted, from a geometrical point of view, to the damaged bone parts.

The shapes and dimensions of the 3D representation of the implant will be modified in order to replace, on the 3D representation, the injured bone part at the surface of the lateral condyle of the distal end of the femur and the lateral plateau of the proximal end of the tibia by the 3D representation of the implant in order to determine the limitations of the implant and also the limitations of the anchoring of the implant in the lateral femoral condyle and in the lateral tibial plateau in such a way that the implant is the correct and personalized representation of the subtracted and damaged bone parts.

The implant is intended to be used at the interface of two bones parts cooperating with each other, namely the lateral condyle 21 of the distal end of the femur and the lateral plateau 31 of the proximal end of the tibia.

Moreover, once the 3D representation of the implant 50 has been positioned on the placement sites of the injured bone parts and the modifications of the dimensions and the adjustment of the shape of the implant have been carried out in order to correspond to those damaged bone parts to be treated, the outer surface of the implant anchored in the lateral condyle 21 of the distal end of the femur and the outer surface of the implant anchored on the lateral plateau of the proximal end of the tibia will be determined, the two surfaces being functional surfaces.

Figure 8:
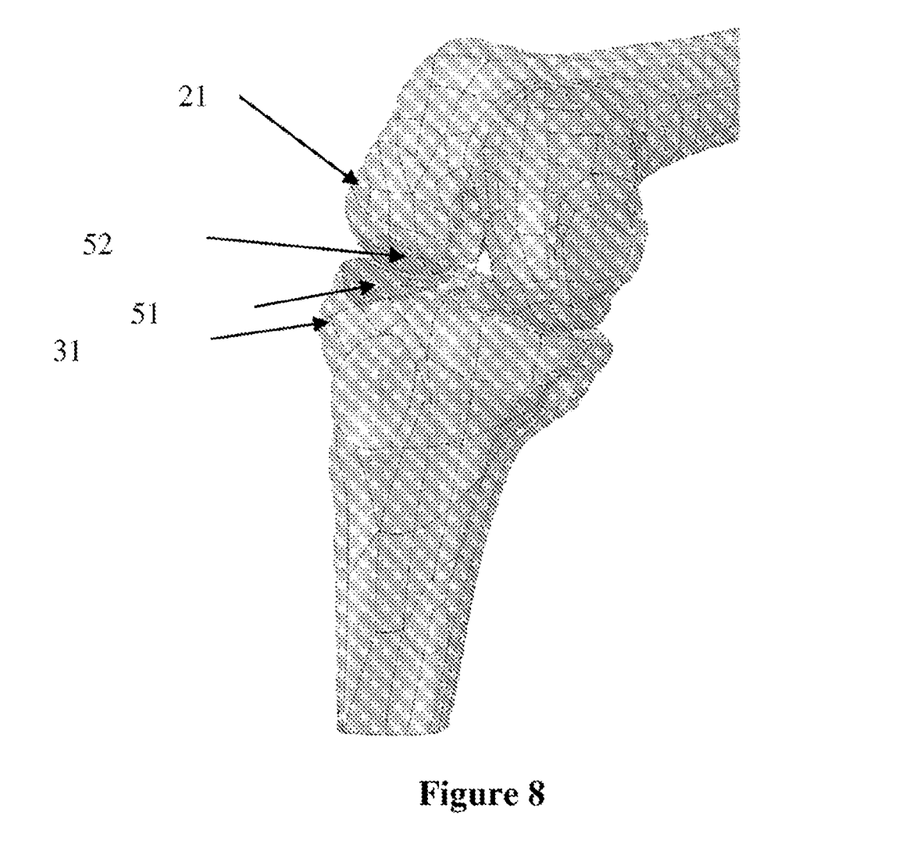
FIG. 8 is a perspective view of a 3D representation of the tibiofemoral joint and a 3D representation of an implant designed specifically for the damaged bone parts, the functional surfaces of the implant having been determined.

Thus, as shown in FIG. 8, the functional surface 51 of the 3D representation of the implant anchored on the lateral plateau 31 will be determined according to the conjugate surface of the lateral condyle 21 with which it cooperates, this in order to ensure the articulation between the lateral plateau 31 and the lateral condyle 21, the conjugate surface corresponding to the functional outer surface 52 of the implant.

In the same way, the functional surface 52 of the 3D representation of the implant anchored on the lateral condyle 21 will be determined according to the conjugate surface of the tibial plateau 31 with which it cooperates, this in order to ensure the articulation between the lateral plateau 31 and the lateral condyle 21, the conjugate surface corresponding to the functional outer surface 51 of the implant.

The articulation between the lateral condyle 21 of the distal end of the femur and the lateral plateau 31 of the proximal end of the tibia is advantageously recovered.

Figure 9:
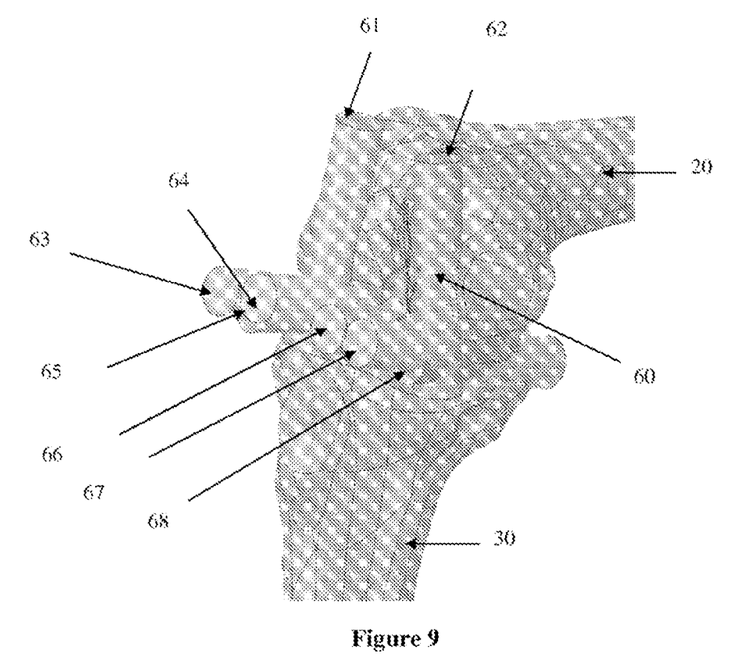
FIG. 9 is a 3D representation of the tibiofemoral joint and a 3D representation of an implant having geometric shapes substantially corresponding to the local modifications.

FIG. 9 is the 3D representation of the tibiofemoral joint and a 3D representation of an implant having geometric shapes corresponding substantially to the local modifications.

In the same way as before, the images of the proximal end 30 of the tibia and of the distal femoral end 20 have been acquired by magnetic resonance imaging and have subsequently been segmented and modeled in 3D on a computer, the transmission of said images being made in STL format. A 3D image of the proximal tibial end 30 and of the distal femoral end 20 is thus acquired.

The 3D representation of an ancillary 60 comprising cutting axes, each determined by the longitudinal axis of a guide tube of a tool such as a drill defining work zones, has been superposed on the 3D representation on a placement site at the surface of each damaged bone part. The cutting axes of the 3D representation of this ancillary correspond to the local modifications to be made to the surface of each damaged bone part.

Thus, the 3D representation of the ancillary 60 has eight tubular elements 61, 62, 63, 64, 65, 66, 67, 68, each having a longitudinal axis, each longitudinal axis of each of the tubular elements coinciding with only one of the eight work axes determined by the practitioner on the 3D representation of the tibiofemoral joint, these work axes corresponding to the local modifications to be made to the damaged bone parts.

For example, the longitudinal axis of the tubular element of the 3D representation of the ancillary will correspond substantially to the recess passing through the lower part of the lateral condyle of the distal femoral end.

The longitudinal axis of the tubular element 62 of the 3D representation of the ancillary will correspond substantially to the recess passing through the lower part of the medial condyle of the distal femoral end.

The longitudinal axis of the tubular element 63 of the 3D representation of the ancillary will correspond substantially to the recess directed toward the lateral cheek of the trochlea.

The longitudinal axis of the tubular element 64 of the 3D representation of the ancillary will correspond substantially to the recess directed toward the juxtaposition zone between the posterior part of the lateral condyle and the lateral glenoid surface of the tibial plateau.

The longitudinal axis of the tubular element 66 of the 3D representation of the ancillary will correspond substantially to the recess directed toward the juxtaposition zone between the posterior part of the medial condyle and the medial glenoid surface of the tibial plateau.

The longitudinal axis of the tubular element 65 of the 3D representation of the ancillary will correspond substantially to the recess directed toward the median groove (or furrow) of the trochlea.

The longitudinal axis of the tubular element 67 of the 3D representation of the ancillary will correspond substantially to the recess directed toward the medial cheek of the trochlea.

The longitudinal axis of the tubular element 68 of the 3D representation of the ancillary will correspond substantially to the recess directed toward the pre-spinal surface of the upper face of the proximal end of the tibia.

Figure 10:
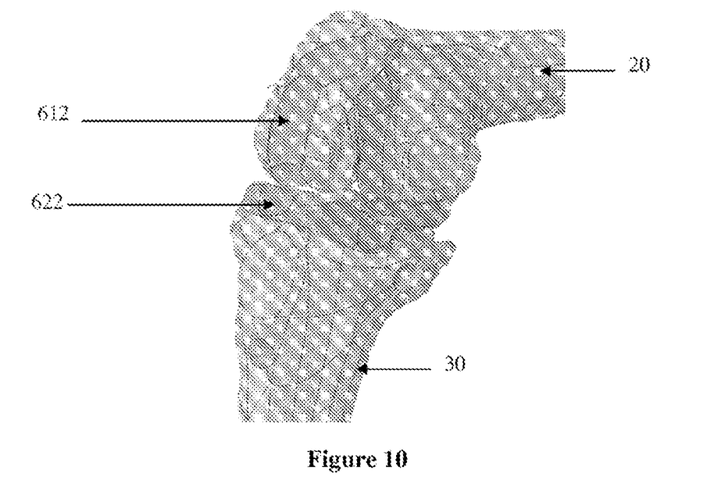
FIG. 10 is a 3D representation of the tibiofemoral joint and of the placement site once the shapes and dimensions and also the functional surfaces of the 3D representation of the implant are determined.

Thus, as shown in FIG. 10, with local modifications made to the 3D representation of the tibiofemoral joint, the shapes and dimensions of the anchoring surface of the implant will be able to be determined according to the shape and dimensions of the local modifications thus made, here the recesses 612, 622 formed on the 3D representation of the tibiofemoral joint, by subtraction of the volume of the implant 60 such that the anchoring surface of the implant permits the anchoring of the implant on the damaged bone part.

Once the anchoring surface has been formed, the outer surface of the implant will be determined.

The functional surface of the 3D representation of the implant anchored on the distal femoral end 20 will be determined according to the conjugate surface of the proximal tibial end 30 with which it cooperates, this in order to ensure the articulation between the distal femoral end 20 and the proximal tibial end 30, the conjugate surface corresponding to the functional outer surface of the implant.

In the same way, the functional surface of the 3D representation of the implant anchored on the proximal tibial end 30 will be determined according to the conjugate surface of the distal femoral end 20 with which it cooperates, this in order to ensure the articulation between the distal femoral end 20 and the proximal tibial end 30, the conjugate surface corresponding to the functional outer surface of the implant.

The articulation between the distal femoral end 20 and the proximal tibial end 30 is advantageously recovered by virtue of the knee-resurfacing prosthesis thus obtained and is intended to replace the worn rollers of the condyles which roll, slide and turn on the glenoid surfaces, themselves worn, of the tibial plateaus, and is intended to do so without in any way affecting the mechanical balance of the joint.

The invention claimed is:

1. A method for producing a tailor-made implant intended to be implanted on a placement site of at least one damaged bone part, comprising the following steps:
   i. acquisition of one or more images of at least said damaged bone part;
   ii. graphical 3D representation of the image of at least said damaged bone part acquired at step i.;
   iii. superpositioning of a 3D representation of a standard implant on the 3D representation obtained at step ii., by positioning said standard implant on a placement site at the surface of said at least one damaged bone part, then, modification of the dimensions and/or adjustment of the shape of said standard implant, taking account of at least one parameter of said at least one damaged bone part, then modification of the outer surface of said standard implant, the modification of the outer surface of said standard implant being such that said standard implant thus positioned on said placement site is imparted an outer surface which is:
      a functional outer surface, when said tailor-made implant is intended to be used at the interface of two bone parts cooperating with each other, said functional surface being determined in such a way that, being at least partially in contact with a conjugate surface of the other bone part with which said damaged bone part cooperates, it ensures the articulation of said bone parts, the determination of said functional surface is performed while the two bone parts are in a functional position in the graphical 3D representation, an acquisition of one or more images of said two bone parts having been performed at step i; and
   iv. realization of the tailor-made implant from the definitive parameters of said implant obtained at step iii.

2. The production method of claim 1, wherein said superpositioning of a 3D representation of a standard implant on the 3D representation obtained at step ii. is performed by fading.

3. The production method of claim 1, wherein, before the step of determination of the outer surface of said implant, the step iii) comprises a step in which at least one local modification directly on a placement site of the graphical 3D representation of said at least one damaged bone part, determination of the shape and dimensions of said anchoring surface of an implant depending on the shape and the dimensions of said at least one local modification performed on said graphical 3D representation, said anchoring surface permitting the anchoring thereof on said damaged bone part.

4. The production method of claim 1, wherein said implant is a part of a medical device intended to be implanted.

5. The production method of claim 1, wherein said conjugate surface corresponds to the outer surface of another implant received at the surface of said other bone part cooperating with said damaged bone part.

6. The production method of claim 1, wherein the outer surface of said implant is determined by removing material from a solid surface of the graphical representation of the implant.

7. The production method of claim 6, wherein, at step iii. a), the portion of the implant to be removed is determined by subtracting the only graphical representation of said at least one bone part to be repaired obtained at step ii. from the graphical representation representing the combination of bone part and standard implant positioned on its placement site.

8. The production method of claim 1, wherein the outer surface of said implant is determined by addition of material.

9. The production method of claim 1, wherein, at step iii. b), said local modification is a continuous recess.

10. The production method of claim 1, wherein, at step iv), said implant is formed by additive manufacture.

11. The production method of claim 1, further comprising a supplementary step of additive manufacture of said at least one bone part acquired at step ii.

* * * * *